United States Patent [19]
Higashikawa

[11] Patent Number: 5,830,193
[45] Date of Patent: Nov. 3, 1998

[54] SYRINGE

[76] Inventor: Tetsuro Higashikawa, 21-5, Kamimeguro 5-chome, Meguro-ku, Tokyo, Japan

[21] Appl. No.: 557,099
[22] PCT Filed: Dec. 19, 1994
[86] PCT No.: PCT/JP94/02138
    § 371 Date: Dec. 6, 1995
    § 102(e) Date: Dec. 6, 1995
[87] PCT Pub. No.: WO95/17916
    PCT Pub. Date: Jul. 6, 1995

[30] Foreign Application Priority Data

| Dec. 28, 1993 | [JP] | Japan | 5-334713 |
| Sep. 19, 1994 | [JP] | Japan | 6-223480 |
| Sep. 29, 1994 | [JP] | Japan | 6-235078 |

[51] Int. Cl.⁶ ................................... A61M 5/00
[52] U.S. Cl. .................. 604/191; 604/218; 604/240; 604/242; 604/90
[58] Field of Search ................. 366/235; 222/195; 206/219–221; 604/82–85, 89–92, 218, 191, 199, 200, 236–238, 240–243, 416, 231

[56] References Cited

U.S. PATENT DOCUMENTS

| 3,699,961 | 10/1972 | Szpur. | |
| 3,828,775 | 8/1974 | Armel | 604/200 |
| 3,908,654 | 9/1975 | Lhoest et al. | 604/200 |
| 4,248,227 | 2/1981 | Thomas | 604/200 |
| 4,479,801 | 10/1984 | Cohen | 604/238 |
| 4,496,344 | 1/1985 | Kamstra. | |
| 4,599,082 | 7/1986 | Grimard. | |
| 4,613,326 | 9/1986 | Szwarc | 604/238 |
| 4,720,285 | 1/1988 | Pickhard. | |
| 4,792,329 | 12/1988 | Schreuder. | |
| 4,820,286 | 4/1989 | van der Wal | 604/191 |
| 4,929,230 | 5/1990 | Pfleger | 604/238 |
| 4,938,745 | 7/1990 | Sagstetter | 604/263 |
| 5,069,225 | 12/1991 | Okamura | 604/243 |
| 5,112,318 | 5/1992 | Novacek et al. | 604/240 |
| 5,261,881 | 11/1993 | Riner. | |
| 5,383,864 | 1/1995 | van den Heuvel. | |
| 5,403,288 | 4/1995 | Stanners | 604/240 |
| 5,468,803 | 11/1995 | Takahashi et al. | 524/553 |
| 5,489,266 | 2/1996 | Grimard | 604/191 |
| 5,535,746 | 7/1996 | Hoover et al. . | |
| 5,611,785 | 3/1997 | Mito et al. | 604/239 |

FOREIGN PATENT DOCUMENTS

| 0 112 574 | 7/1984 | European Pat. Off. . | |
| 0 172 990 | 3/1986 | European Pat. Off. . | |
| 0 311 324 | 4/1989 | European Pat. Off. . | |
| 0 399 234 | 11/1990 | European Pat. Off. . | |
| 0 415 867 | 3/1991 | European Pat. Off. . | |
| 0568321 | 11/1993 | European Pat. Off. | 604/236 |
| 60-72561 | 4/1985 | Japan . | |
| 62-501268 | 5/1987 | Japan . | |
| 62-58745 | 12/1987 | Japan . | |
| 3-58434 | 6/1991 | Japan . | |
| 9118640 | 12/1991 | WIPO | 604/200 |

*Primary Examiner*—Ronald K. Stright, Jr.
*Attorney, Agent, or Firm*—McDermott, Will & Emery

[57] ABSTRACT

A syringe in which one or more injectable materials are filled, comprises a cylinder or barrel in which a front partition stopper, which can be fixed or movable depending on the embodiment, and one or more intermediate partition stoppers are slidably disposed. In the simplest arrangement, a single intermediate partition stopper is disposed between the front partition stopper and a rear piston, to define first and second chambers within the cylinder in which first and second injectable materials can be respectively filled. An outer periphery of the intermediate partition stopper is provided with a plurality of circular lips between which at least one peripheral groove is defined. One of the first and second chambers is communicated with peripheral groove or grooves of the intermediate partition stopper by small passages to allow the first medicine, which is in liquid form, to enter and fill the groove or grooves and exclude air and bacteria therefrom. A transfer passage or passages are arranged in the wall of the cylinder to allow the first and second medicines to mix as the partition stopper is moved forward in response to the rear piston being forced into the cylinder.

2 Claims, 12 Drawing Sheets

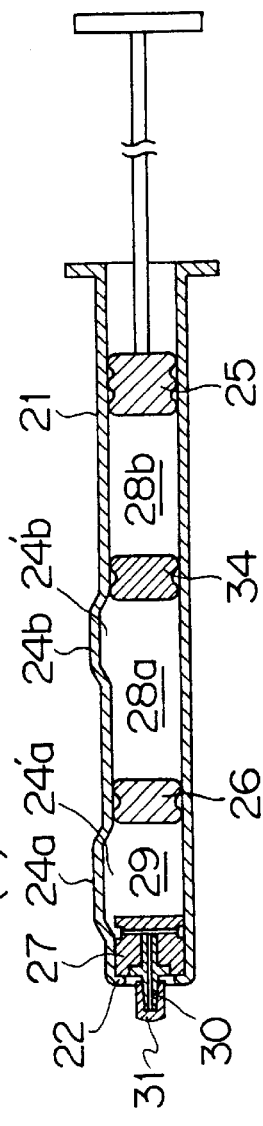
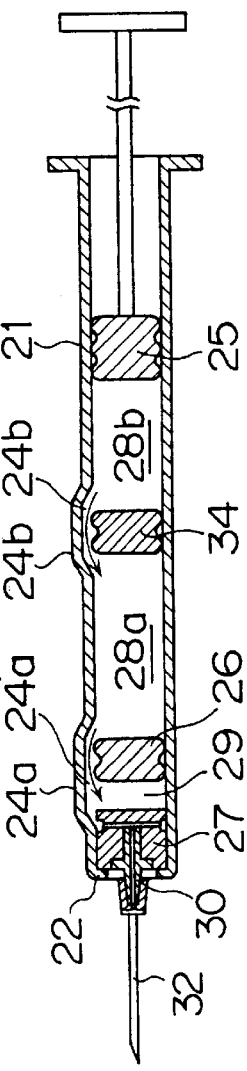
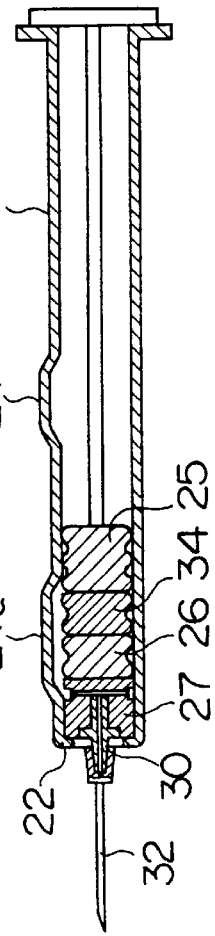
FIG. 9(a)  FIG. 9(b)  FIG. 9(c)
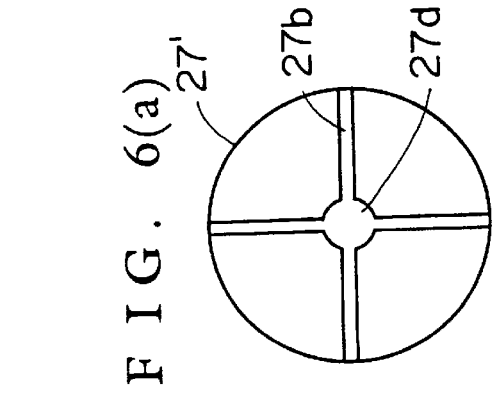
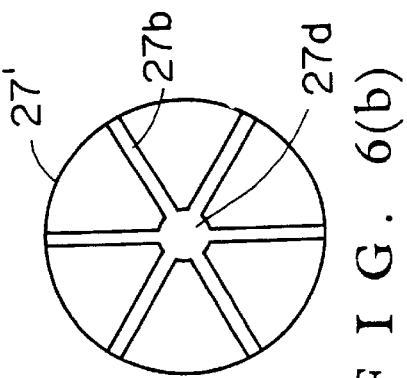
FIG. 6(a)  FIG. 6(b)

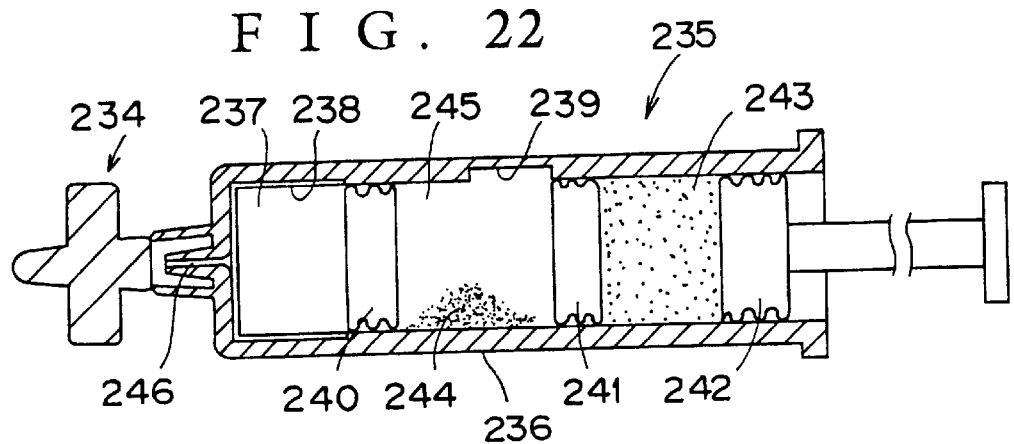
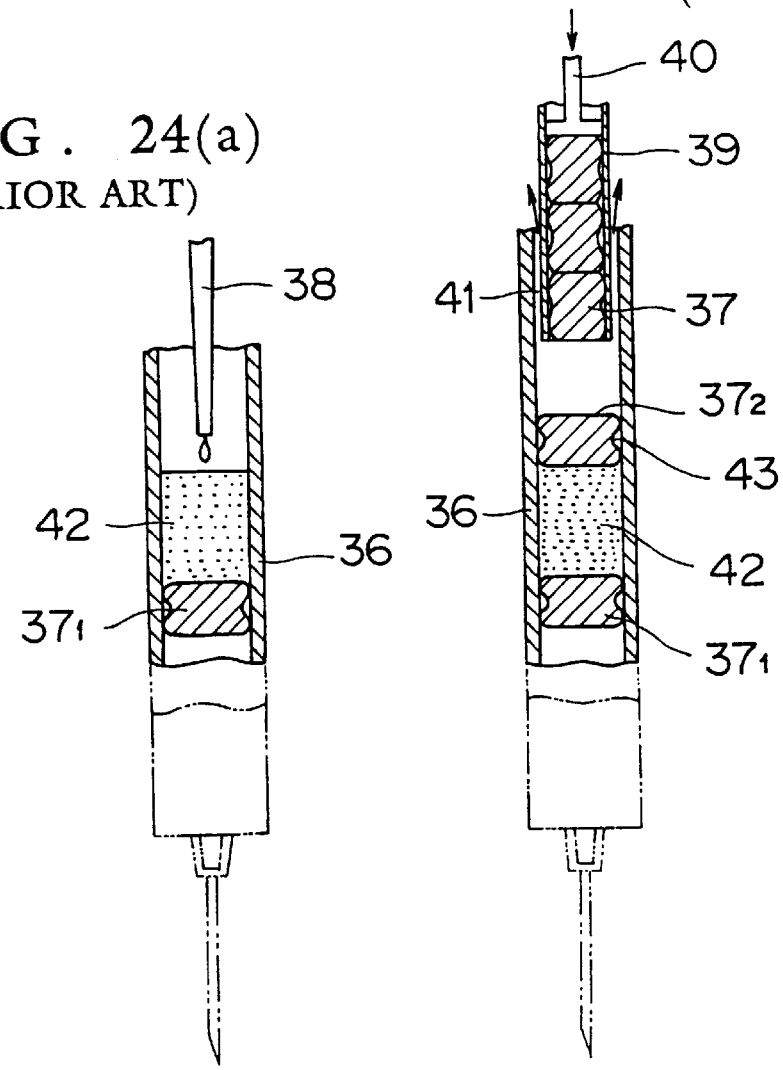

FIG. 25
(PRIOR ART)
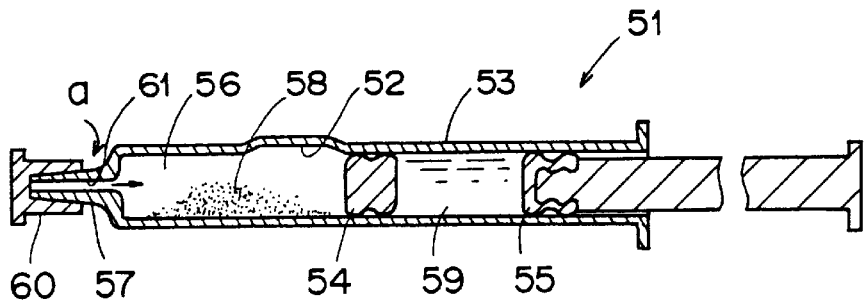
FIG. 23(a)
(PRIOR ART)
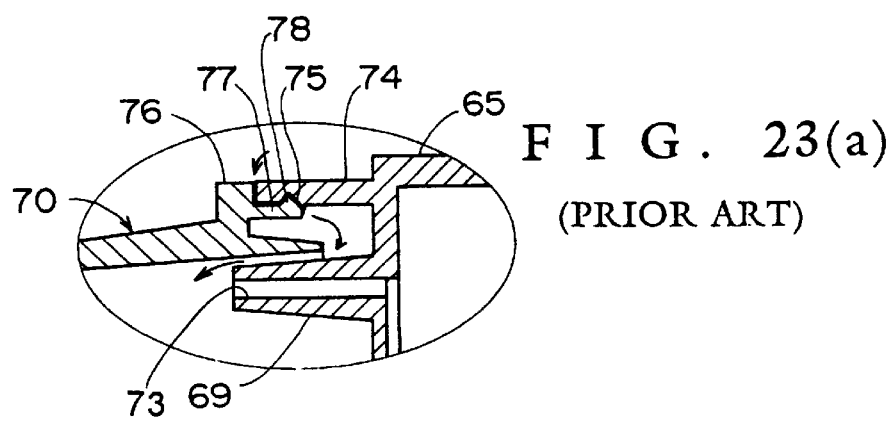
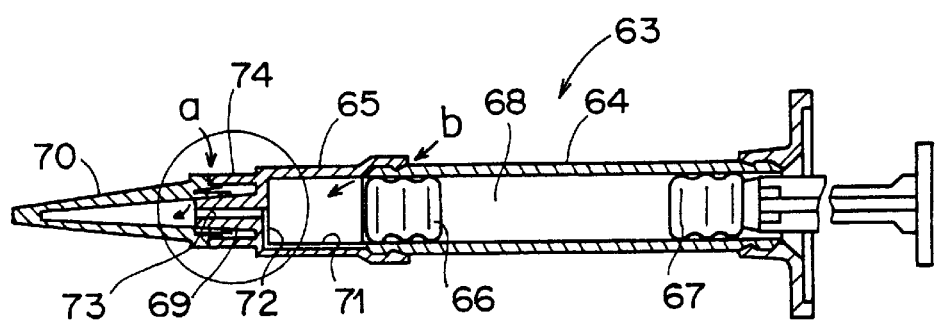
FIG. 23(b)
(PRIOR ART)

SYRINGE

TECHNICAL FIELD

The present invention relates to a kit style syringe having a syringe cylinder which is previously filled with medicine, and more particularly to an improved sealing arrangement which prevents invasion of bacteria and vapor during storage and sterilization.

BACKGROUND ART

Japanese Patent Publn. No. 62-58745 disclose a kit style syringe which, as shown in FIG. 23 can be previously filled with medicine and permits injection to be easily performed by only attaching a syringe needle. As shown in FIG. 23, a syringe 63 includes a glass cylinder body 64, a barrel 65 of synthetic resin fixedly fit into the front of the cylinder body 64, and a cap 70 of synthetic resin mounted on a syringe needle connection portion 69 at the tip of the barrel 65. A slidable partition stopper 66, a piston 67 and a medicine solution 68 filled therebetween are arranged in the cylinder body 64. The barrel 65 and cylinder 64 constitute a syringe cylinder.

The barrel 65 has an inner diameter equal to that of the cylinder body 64. On the inner wall of the barrel 65 are formed a longitudinal groove 71 and a delivery groove 72 extending from the groove 71 to a discharge hole 73 of the needle connection portion 69. In operation, when a piston 67 is pushed, the partition stopper 66 moves into the barrel 65. The medicine 68 is then introduced into the discharge hole 73 through the grooves 71 and 72. A syringe needle is lure-locked with the needle connection portion 69 which is tapered, i.e., surely fixed there by elasticity peculiar to the resin from which the needle connection portion 69 is made.

The cap 70 is fixedly fitted on an external cylinder 74 formed around the needle connection portion 69 of the barrel 65 as seen in the enlarged view shown FIG. 23. Specifically, a peripheral groove 75 is formed on the side of the inner wall of the external cylinder 74. A protrusion 78 of a circular engagement hem 77 extending from a flange of the cap 70 is engaged with the peripheral groove 75 so that the flange 76 intimately abuts against the external cylinder 74. The cap 70 serves to prevent the invasion of dust during safekeeping.

However, the syringe 63 described above can inject only one kind of medicine. Where two or more kinds of injection agents or medicines, e.g., agents A and B should be mixedly injected, these two kinds of injection agents must be mixed previously. In this case, even where the agents A and B exist solely, respectively, and can be stably preserved for a long time, it may be difficult to maintain the stability in the mixed state of A+B.

A syringe which permits two kinds of medicines to be separately preserved has been proposed in Japanese Utility Mode Preliminary Publn. 3-58434. This syringe (not shown) has a structure similar to that explained above in connection with the above Japanese Patent Publn. 62-58745, in which another partition stopper is arranged between the partition stopper 66 and the piston 67 to permit two kinds of injection agents to be accommodated. This syringe, in which the shape of a passage in the barrel is slightly modified, has basically the same structure as that of the syringe disclosed in FIG. 23.

In any syringe described above, however, the barrel 65 must be fabricated as a separate component and attached to the tip of the cylinder 64. Such a syringe is too expensive to manufacture because the structure of the barrel is complicated and requires high accuracy.

Meanwhile, filling of medicine solution and insertion of partition stoppers in the syringe are carried out by the vacuum filling/stopping technique shown in FIGS. 24(a) and 24(b). In this technique, first, as shown in FIG. 24(a), a front partition stopper $37_1$ is inserted into the front of the cylinder 36 and thereafter the first medicine solution 42 is injected from a solution nozzle 38. In this case, the interior of the cylinder 36 is evacuated to prevent mixing of air in the medicine solution 42.

Next, as shown in FIG. 24(b), a partition stopper 37 pushed into a metallic cylindrical tube 39 by reducing its diameter is instantaneously pushed out into the cylinder 36 using a push rod 40. At this time, air between the medicine solution 42 and by way of an intermediate partition stopper $37_2$ slips out by way of a slit 41 between the cylindrical tube 39 and the cylinder 36 as indicated in arrows. A second medicine solution is injected in an evacuated state. Thus, a separate-injection style syringe can be fabricated. The conventional syringes, however, have a defect that when the cylinder 36 is filled with the medicine solution 42, air is apt to remain in a peripheral groove 43 of the intermediate partition stopper $37_2$. Further, the conventional syringes have also the following defect. Where the air remains in the peripheral groove 43, when the intermediate partition stopper $37_2$ moves in a vacant chamber of the barrel 65 in FIG. 23, air will be mixed in the medicine solution 42. For this reason, the syringe must be once pulled out from a human body to evacuate. When bacteria are mixed in the air remaining in the peripheral groove 43, they will invade the medicine solution 42.

On the other hand, Japanese Patent Preliminary Publn. 60-72561 proposes a syringe 51 as shown in FIG. 25. This syringe includes a glass cylinder 53 having a swelling groove 52 in the intermediate portion, a rubber partition stopper 54 arranged behind the groove 52 within the cylinder 53, a piston 55 behind the partition stopper 54, a front chamber 56, i.e., medicine powder 58 accommodated between the syringe needle connection portion 57 at the front and the partition stopper 54, a rear chamber (i.e., a dilution solution 59 filled between the partition stopper 54 and the piston 55), and a rubber cap 60 covering the syringe needle connection portion 57.

The rubber cap 60 shuts a discharge hole 61 of the syringe needle connection portion 57 to prevent vapor absorption by the medicine powder 58 during storage of the syringe 51. In using the syringe 51, the piston 55 is pushed to move the piston 55 to the groove 52 of the cylinder 53. As a result, the diluted solution 59 is injected into the front chamber 56 so that it will be mixed with the medicine powder 58 by stirring.

These syringes 51 and 63 described above permit persons engaged in medical treatment to remove the caps 60 and 70, mount a syringe needle and immediately give a patient an injection without labor of filling medicine solution. As compared with the conventional syringes, these syringes can prevent inconveniences of pollution of a syringe needle in sucking medicine solution, mixing of glass pieces due to ampule cutting in filling the medicine solution and mixing of minute fragments of rubber or invasion of bacteria in thrusting the needle through the rubber stopper of a vial.

The syringe 51, 63 is required to conduct pre-sterilization and post-sterilization under rules of the FDA in U.S.A. The pre-sterilization is carried out for each of the components in the process of making the syringe, and the post-sterilization is carried out upon completion of assembling the components. The post-sterilization is carried out by e.g. spraying of flowing steam at 120° for 20 minutes. Thereafter, the syringe is wrapped. The wrapping is performed in an aseptic room by using a sterilization sack made of vinyl and further vacuum packing the sterilization sack. After the wrapping, the syringes must be preservable for two or three years.

However, the syringe described above suffers from the following serious problem. In addition to that the cap 60, 70 is apt to come off, in the post-sterilization, steam will invade from an opening of the cap 60, 70 and a small opening between the barrel 65 and the cylinder body 64 as indicated by character a and b in FIGS. 23 and 25. Bacteria are also apt to invade. This is because a minute opening will occur even when the barrel 65 made of synthetic resin and glass cylinder 64 made of glass are pressure-coupled with each other. Further, even if the post-sterilization is successful, when a small hole is made in the sterilization sack during storage after the wrapping or the bacteria killing in the sack is not complete, bacteria will invade from openings of the cap 60, 70 and the barrel 65.

In view of the above points, in order to realize three rules of the kit style syringe, i.e., reduction in burden, prevention of mixing of alien substance and destruction of bacteria pollution in preparing medicine, the present invention intends to provide a syringe with excellent sealing performance which can prevent invasion of bacteria and others during a long preserving time or the sterilization step using flowing steam.

SUMMARY OF THE INVENTION

In order to attain the above object, the present invention adopts a first configuration comprising: a cylinder having openings on both ends and a communicating passage provided near the one opening in an axial direction and from whose other opening a piston is inserted; a partition stopper which is slidable within the cylinder and defines a plurality of chambers in the cylinder; an elastic end partition having a passage in a radial direction is fitted on the one opening side of the cylinder and guided to the communicating passage and another passage in an axial direction communicating with the passage; and a rigid syringe connection portion is fitted into the passage in an axial direction of the end partition. The syringe needle connection portion may have rotation stopping protrusions extending in a radial direction and the end partition may have fitting grooves corresponding to the rotation stopping protrusions.

In the first configuration, the elastic partition end is pressed into the front end of the rigid cylinder to make intimate contact with each other, thus preventing invasion of water and bacteria into the cylinder. The rigid syringe needle connection portion is pressed into the passage in an axial direction of the elastic partition end to make intimate contact with each other, thus similarly preventing water or bacteria into the cylinder. The rotation stopping protrusions of said syringe needle connection portion are fitted into the fitting grooves of the partition end, thus preventing rotation of the syringe needle connection portion in lure-locking connection of said syringe needle.

As another means, the present invention adopts, in a syringe in which medicine solution is filled between a partition stopper arranged slidably in a cylinder and a rear piston, and in the outer periphery, a plurality of circular lips and a peripheral groove between said plurality of lips are formed, a second configuration wherein a communicating portion communicating the medicine solution with said peripheral groove is formed. The peripheral grooves may be formed in the rear piston and a communicating portion communicating the grooves with the medicine may be formed in said rear piston. The communicating portion may be communicating grooves formed in the circular lips of the partition stopper or said rear piston.

In accordance with the second embodiment of the present invention, the peripheral groove of the partition stoppers or piston is filled with the medicine solution. For this reason, no air is left in the peripheral groove and there is no fear of bacteria in the air invading the cylinder. Where two partition stoppers are arranged in the cylinder, the front partition stopper is first inserted in the cylinder and the first medicine solution is injected under ventilation. Next, the second intermediate partition stopper is introduced using the vacuum filling/stopping technique. The medicine is filled in the peripheral groove of the intermediate partition stopper to extrude air in the peripheral groove. Thus, the second medicine solution is injected. Where the intermediate partition stopper is mounted in a reverse direction, in injection of the second medicine solution, air in the peripheral groove from the communicating portion (communicating groove) is absorbed by ventilation.

As still another means, the present invention adopts, in a syringe including a syringe needle connection portion and an external cylinder for protection outside the syringe needle connection portion which are formed at the tip of a cylinder made of synthetic resin, a third configuration that a tip hermetic-sealing portion for hermetically sealing the syringe needle connection portion in the external cylinder is integrally formed at the tip of the external cylinder. The tip hermetic-sealing portion may include a head fixed at the tip of the external cylinder through a circular recess groove, and a twisting plate extended from the head. Further, said cylinder may be a resin-integral type cylinder in which the partition stopper and the rear piston are slidable, and a communicating groove for introducing medicine solution successive to a discharge hole of a syringe needle mounting portion is formed in a front vacant chamber of the cylinder. The front vacant chamber partitioned by the partition stopper may be sealed with gas. The material of the cylinder is made of amorphous polyolefin or the like.

In the third configuration, the syringe needle connection portion is surrounded by the external cylinder and the tip hermetic-sealing portion so that it is completely sealed. By twisting the twisting plate, the tip hermetic-sealing portion can be cut from the circular recess groove between the head and the tip of the external cylinder. Further, in unsealing the tip hermetic-sealing portion, the gas pressure in the cylinder and the front partition stopper jointly stop invasion of bacteria from the syringe needle connection portion. The resin integral style cylinder can solve invasion of vapor from the cylinder intermediate portion of the barrel style cylinder. Since the amorphous polyolefin can be easily molded, the communicating groove can be easily and surely formed in the cylinder, and the cylinder can be burned up (viz., incinerated).

BRIEF DESCRIPTION OF DRAWINGS

FIG. 1(a) is a sectional view showing the structure, FIG. 1(b), FIG. 1(c) are sectional views showing the operation and FIG. 1(d) is a sectional view taken along section line I—I of FIG. 1(a).

FIGS. 6(a) and 6(b) are back views of the end partition of FIG. 5; wherein FIG. 6(a) shows a first example, and FIG. 6(b) shows a second example.

FIGS. 7(a) and 7(b) show another example of the syringe needle connection portion; wherein FIG. 7(a) is a front view and FIG. 7(b) is a sectional view taken along section line IV—IV of (a).

FIGS. 8(a) to 8(c) show a separate injection type syringe filled with two kinds of injection agents; wherein FIG. 8(a) is a sectional view showing the structure, FIG. 8(b) and FIG. 8(c) are sectional views showing the operation.

FIGS. 9(a) to 9(c) show a mixing type syringe using two kinds of injection agents; wherein FIG. 9(a) is a sectional view showing the structure and FIGS. 9(b) and (c) are sectional views showing the operation.

FIGS. 18(a) and 18(b) show a sealing structure; wherein FIG. 18(a) is a plan view and FIG. 18(b) is a side view partially sectioned in unsealing.

FIG. 22 is a longitudinal sectional view showing a syringe equipped with a sealing structure.

FIGS. 23A and 23B are longitudinal sectional views wherein FIG. 23A shows, in enlarged form, the portion which is circled in FIG. 23B, and which depicts one example of a conventional syringe. FIG. 23(a) is an exploded view of a portion of FIG. 23(b).

FIGS. 24(a) and 24(b) show an evacuation filling stopping technique; wherein FIG. 24(a) is a sectional view of the state where the first medicine solution has been injected and FIG. 24(b) is a sectional view of the state where an intermediate partition stopper has been incorporated.

FIG. 25 is a longitudinal sectional view showing a second example of a conventional syringe.

BEST MODE OF CARRYING OUT THE INVENTION

Embodiment 1

Figure 1A:
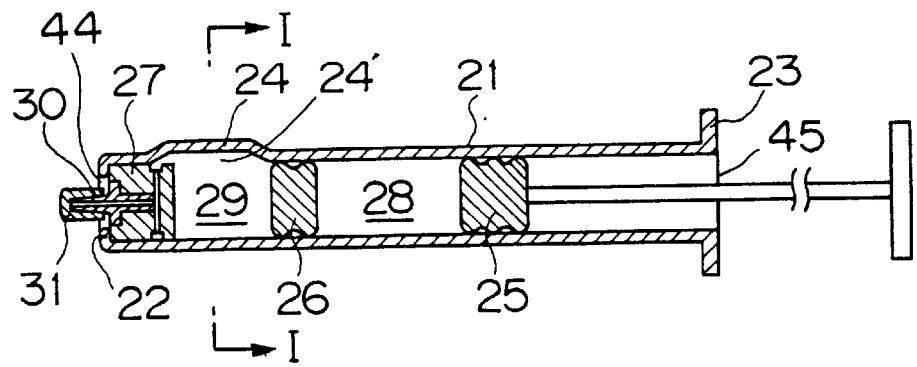
FIGS. 1(a) to 1(d) show a first embodiment of the syringe according to the present invention.
Figure 1B:
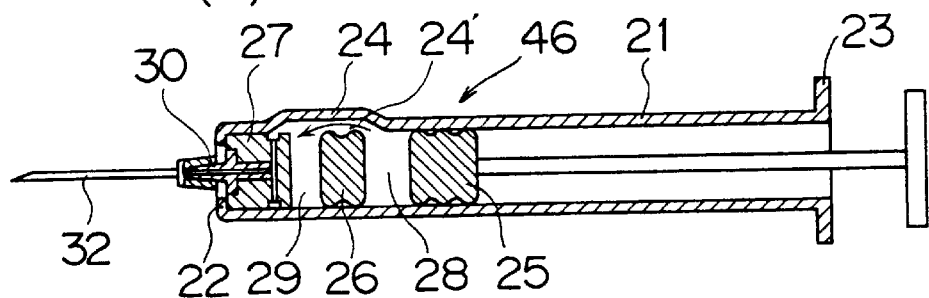
Figure 1C:
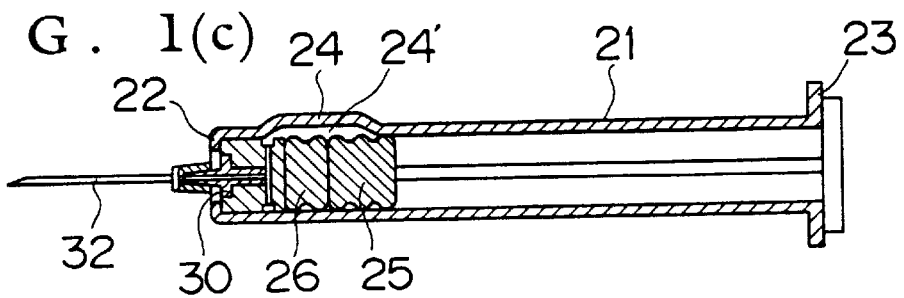
Figure 1D:
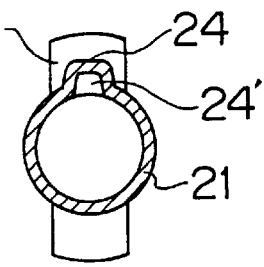

FIGS. 1(a)–(d) show a first embodiment of the syringe according to the present invention. FIG. 1(a) shows the state before use, FIG. 1(b) shows the state during injection, FIG. 1(c) shows the state after injection, and FIG. 1(d) shows the sectional shape of a cylinder. In these figures, reference numeral 21 denotes a cylinder made of glass having openings 44 and 45. The tip of the one opening 44 is a hook-shaped tip 22 whose section is bent in a hook shape. Reference numeral 23 denotes a rear end portion of the cylinder; 24 a swelling portion; and 25 a piston. The swelling portion 24 swells at a portion of the circumference of the cylinder as shown in FIG. 1(d), and forms a communicating path 24' inside it.

In the neighborhood of the center within the cylinder 21, a partition stopper 26 is fit. Both piston 25 and partition stopper 26 are made of flexible resin inclusive of rubber and have lips formed on their outer periphery. The left end of the cylinder 21 in these figures is watertightly (hermetically) closed by an end partition 27. Thus, within the cylinder 21 are formed a first vacant chamber 28 between the piston 25 and the partition stopper 26 and another (second) vacant chamber 29 between the end partition 27 and the partition stopper 26. A syringe needle connection portion 30 is fitted into the end partition 27, and a cap 31 is fitted over the needle connection portion 30.

Figure 2:
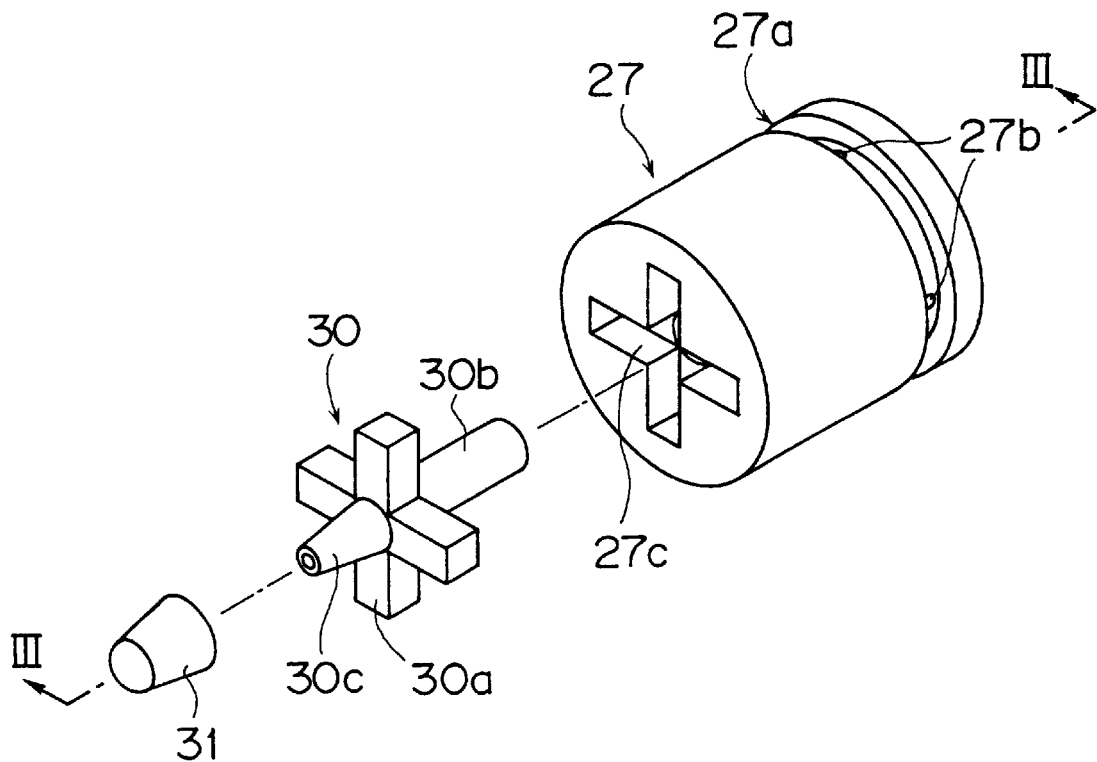
FIG. 2 is an exploded perspective view showing an end partition, a needle connection portion and a cap.
Figure 3:
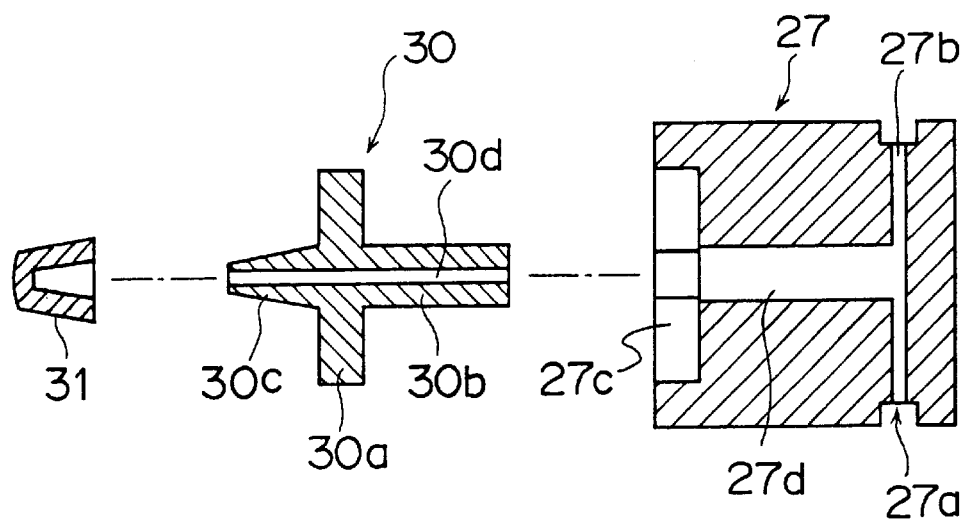
FIG. 3 is a sectional view taken along section line III—III in FIG. 2.

FIGS. 2 to 3 are views showing the details of the end partition 27, the needle connection portion 30 and the cap 31. The end partition 27 is made of rubber or resin having elasticity slightly lower than that of the piston 25 and the partition stopper 26, and is formed in a cylindrical-rod-shape with a U-groove 27a formed on the side of the rear end (near the partition stopper). On the bottom of the U-groove 27a are formed several pores 27b. These several pores 27b, which are made radially towards the center axis of the cylinder, constitute plural passages 27b. On the front surface (on the side of the syringe needle) of the end partition 27, crossed-grooves 27c serving as fitting grooves are formed, and at the center of the crossed shape, an opening 27d is formed along the center axis of the cylinder whose tip is communicated with the above passages 27b. The elastic end partition 27 is intimately fitted onto the side of the opening 44 of the glass rigid cylinder 21 so that there are no gaps.

Figure 4:
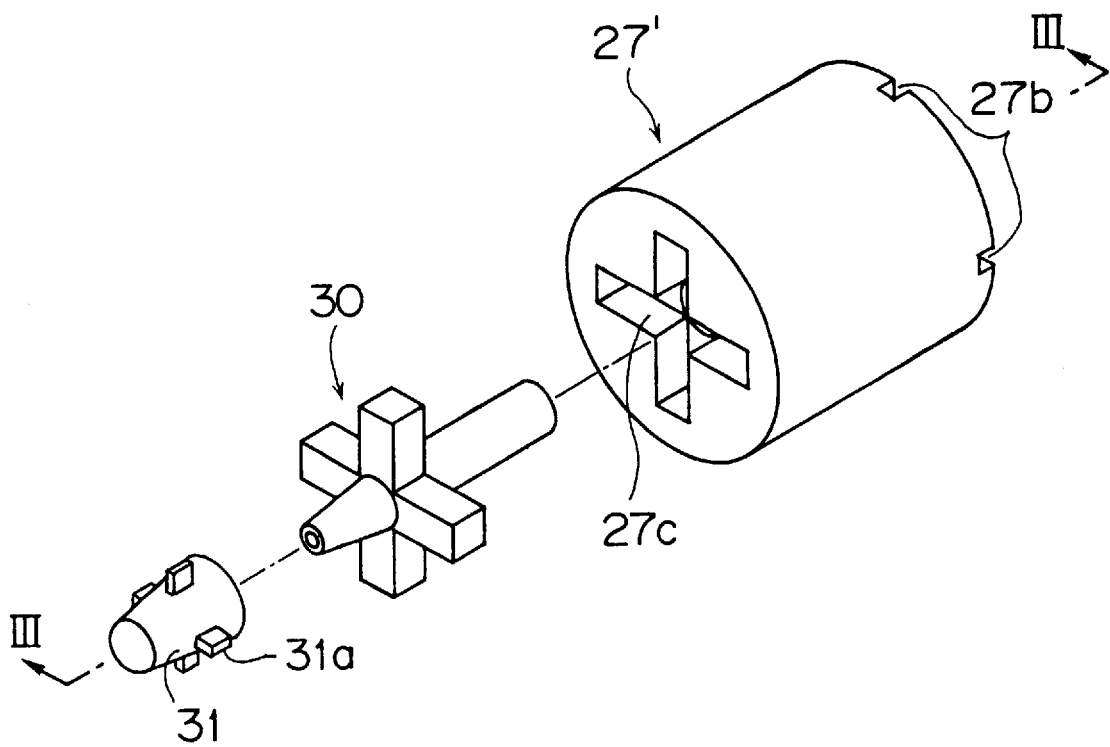
FIG. 4 is a perspective view of a similar example of the partition and the cap.
Figure 5:
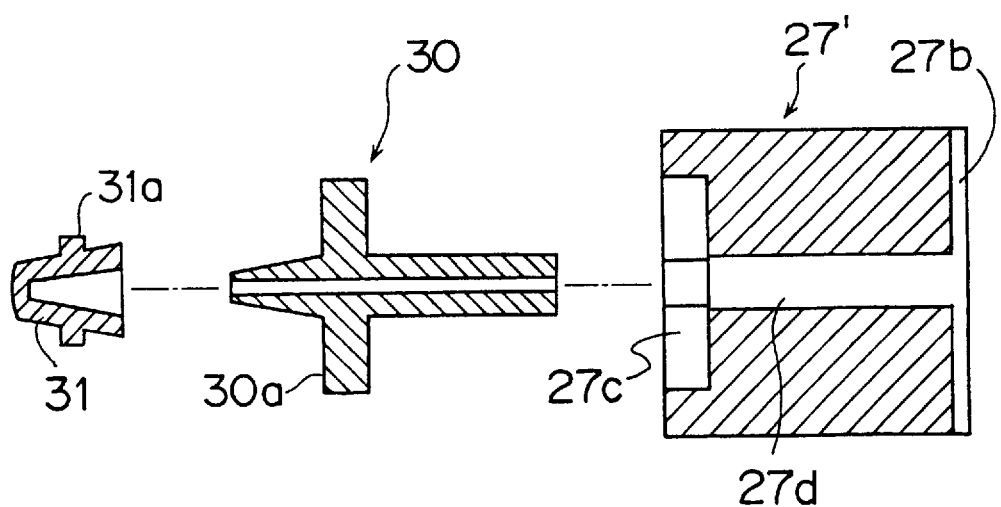
FIG. 5 is a sectional view taken along section line III—III in FIG. 4.

Incidentally, as shown in FIGS. 4 to 6, on the rear surface of an end partition 27', crossed grooves 27b serving as passages may be formed which are communicated with the central opening 27d. In such a configuration, the grooves 27b can be easily formed. In this case, in FIG. 1, the partition stopper 26 abuts on the rear surface of the end partition 27' so that the medicine solution is introduced from the passage 24' of the swelling portion 24 into the grooves 27b. The grooves 27b may be formed radially from the central opening 27d as shown in FIG. 6(a).

In FIG. 2, the syringe needle connection portion 30 integrally includes a crossed frame 30a serving as whirl-stop protrusions fitted onto the crossed grooves 27c, a parallel cylinder 30b extending rightwards from the center of the crossed frame 30a in the figure and a tapered cylinder 30c extended leftwards from the center of the crossed frame 30a, and is made of a rigid body formed by injection molding of plastic. The tapered cylinder 30c is to be connected to the syringe needle. The openings of the cylinders penetrate from the left end of the cylinder 30c to the right end of the cylinder 30b so as to constitute a passage 30d. The cap 31 is made of flexible rubber or the like so as to fit over surely the tapered cylinder 30c and has a shape with a blind tapered hole.

Figure 11:
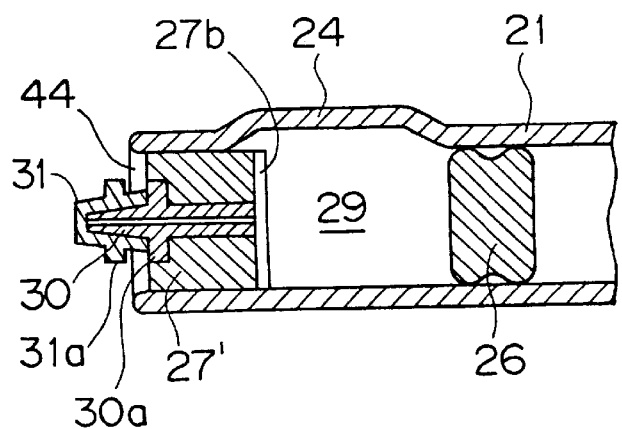
FIG. 11 is a longitudinal sectional view of the second embodiment of the state where the end partition and the cap in FIG. 5 are mounted in the cylinder.

As shown in FIGS. 4 and 5, plural twisting pieces 31a may be protruded from the outer periphery of cap 31. The twisting pieces 31a permit the cap 31 to be tightly fitted over the syringe needle connection portion 30. This enhances the sealing property and permits easy removal. The cap 31 is adapted to have a length that its rear end abuts on the crossed frame 30a of the syringe needle connection portion 30 as shown in FIG. 11, and contributes to improve the sealing property together with the twisting pieces 31a.

With reference to FIG. 1, an explanation will be given of the operation of the syringe 46. The syringe 46, as shown in FIG. 1(a), is maintained in a state where the vacant chamber 28 is filled with injection medicine and the vacant chamber 29 is filled with no injection medicine. In use, first, the cap 31 is removed and the syringe needle 32 is fitted by a lure-locking system. With the syringe needle 32 upwards, when the piston 25 is pushed as shown in FIG. 1(b), the partition stopper 26 is located at the communicating passage 24' of the swelling portion 24. Then, the injection medicine in the chamber 28 moves into the vacant chamber 29. After air in the vacant chamber 29 is exhausted, the syringe needle 32 is inserted a patient. The injection medicine passes from the passages 27b through the passage 30d into the syringe needle 32.

FIG. 1(c) shows the state where injection is completed. The piston 25 is pushed so that the end partition 27, partition stopper 26 and the piston 25 are brought into intimate contact with one another. Then, if the tip (on the side of the syringe needle) of the piston 25 does not reach the interior of the passage 24', the entire injection medicine in the chamber 28 cannot be injected. The passages 27b of the end partition 27 must be located on the passage 24'. In order to satisfy such a condition, the thicknesses of the end partition 27, partition 26 and piston 25 in an axial direction and the length and position of the swelling portion 24 are determined.

Figure 7A:
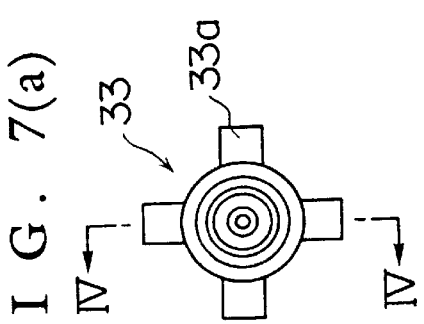
Figure 7B:
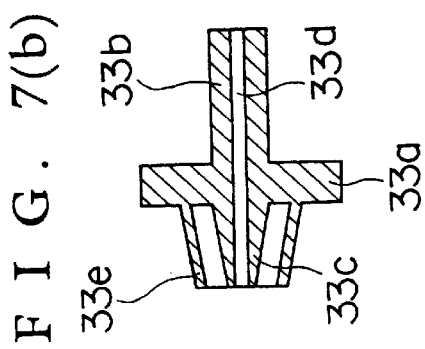

FIGS. 7(a), (b) show another embodiment of the syringe needle connection portion. In this embodiment, a syringe needle connection portion 33 includes a crossed frame 33a, cylinders 33b, 33c and a passage 33d which are those constituting the syringe needle connection portion 30 shown in FIGS. 2 and 3, and further includes an external cylinder 33e for protection outside the tapered cylinder 33c. It should be noted that the tapered cylinders 33c and 30c are connected to the syringe needle 32 by the lure locking system.

Figure 8A:
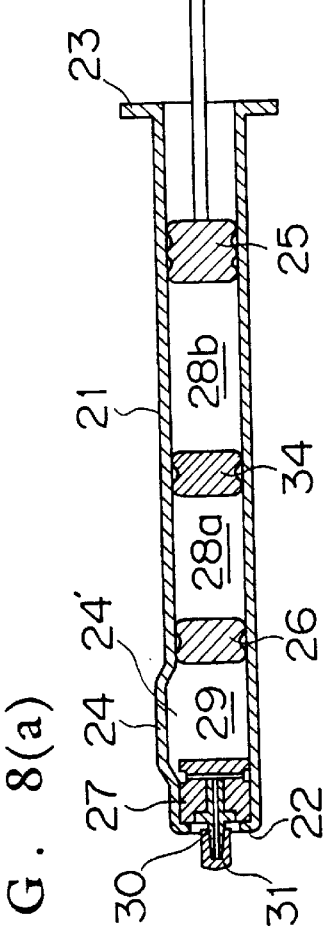
Figure 8B:
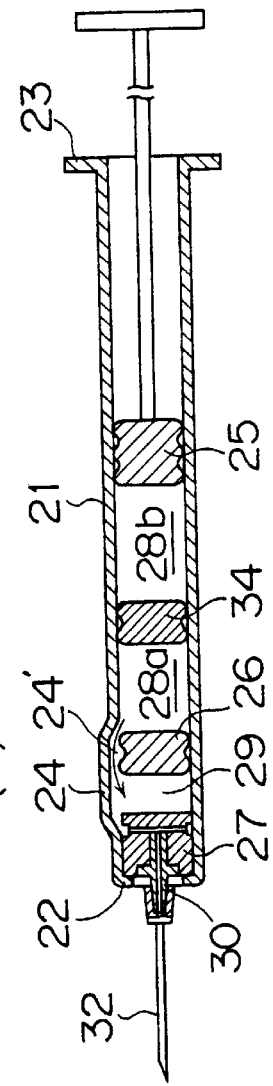
Figure 8C:
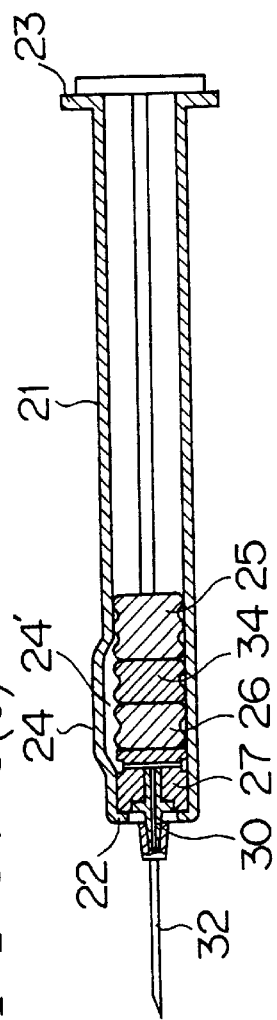

FIGS. 8(a) to 8(c) show an embodiment of a separate type syringe for injecting two injection medicines, i.e., A and B previously put in the syringe in a such a fashion of injecting first medicine A and subsequently medicine B. FIG. 8(a) shows the state where the medicines are preserved; FIG. 8(b) shows the state when injection is started; and FIG. 8(c) shows the state when the injection has been finished.

This embodiment has a configuration in which another partition stopper 34 is inserted between the piston 25 and the partition stopper 26 in the embodiment of FIG. 1 so as to divide the chamber 28 into chambers 28a and 28b. The chambers 28a and 28b are filled with medicines A and B, respectively. At least the chamber 28b is filled with only medicine with no air contained by the vacuum filling system.

With the cap removed from the state of FIG. 8(a), the syringe needle 32 is connected. With the syringe 32 oriented upwards, when the plunger 25 is pushed, the pressure in the chamber 28b increases to push the partition stopper 34.

Thus, the pressure in the chamber 28a increases to push the partition stopper 26 into the side of the communicating passage 24 as shown in FIG. 8(b). Then, the injection medicine within the chamber 28b enters the chamber 29 and air is ejected through the syringe needle. Having confirmed that the air has been removed, injection is carried out. The injection medicine in the chamber 28a is accordingly injected into the body of a patient. When the injection agent in the chamber 28a runs out, the partition stoppers 26 and 34 are brought into intimate contact with each other so that both partitions are located on the communicating passage 24'. The injection medicine within the chamber 28b is injected into the human body through the passage 24'.

FIG. 8(c) shows the state where injection has been finished. In this state, the tip of the piston 25 must be located on the communicating passage 24'. The communicating passages 27b of the end partition 27 must be located in the communicating passage 24'. On the basis of such a condition, the thickness of each partition stopper and the piston and the length and position of the communicating passage 24' are determined.

FIGS. 9(a) to 9(c) show an embodiment of a syringe which can preserve two injection medicines in a divisional manner like FIG. 8, and can inject them after having been mixed (or perform "mixing injection"). The syringe according to the embodiment of FIG. 9 is different from that of FIG. 8 in that two swelling portions 24a and 24b are separated from each other. The partitions 26 and 34 are arranged behind the swelling portions 24a and 24b, respectively. The chamber is divided into two chambers 28a and 28b which are filled with different injection agents.

In use, with the cap 31 removed in the state of FIG. 9(a), the syringe needle 32 is connected. With the syringe 32 upwards, the plunger 25 is pushed. As shown in FIG. 9(b), the partition stopper 34 is located on the communicating passage 24b'. Air within the chamber 28b passes through the communicating passage 24b' to enter the chamber 28a and subsequently the injection agent enters there. The partition stopper 26 also reaches the communicating passage 24a' and air within the chambers 28a and 28b passes through the communicating passage 24a' to leak out slightly from the syringe needle 32. With the entire injection agent within the chamber 28b having been moved into the chamber 28a, the syringe is shaken to mix these two injection agents sufficiently. Thereafter, the air within the chamber 28a is expelled from the syringe. An injection is given to a patient. FIG. 9(c) shows the state when injection has been finished. This state, which is the same as that explained in connection with FIG. 8(c), will not be explained here.

Figure 10:
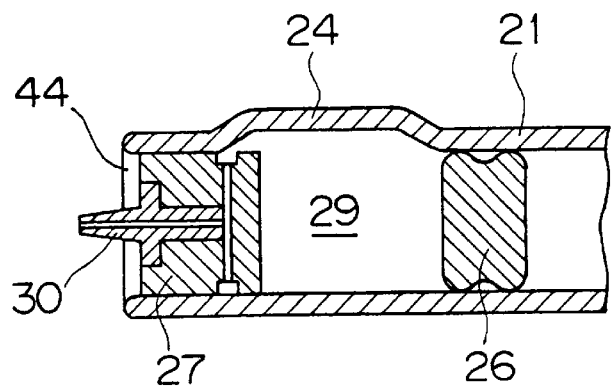
FIG. 10 is a sectional view of the main part showing the other embodiment of a cylinder.

FIG. 10 shows an embodiment of the cylinder 21 having a different shape. This cylinder 21 does not have the hook-shaped tip portion 22 at the opening 44 on the side of the syringe needle, but a straight opening end whose opening diameter is equal to the inner diameter of the cylinder 21. Such a configuration permits the cylinder to be easily fabricated, thus reducing production cost of the cylinder. Where there is the hook-shaped tip portion 22, the end partition 27 is fitted through the opening through which the piston 25 is inserted. The straight shape as shown in FIG. 10 permits the end partition 27 to be directly fit from the opening 44 on the side of the syringe needle, which can be easily implemented. FIG. 11 shows the state where the end partition 27' and the cap 31 equipped with the twisting pieces 31a have been mounted in the cylinder 21.

In accordance with the first embodiment, since the elastic engagement between the cylinder made of glass and the end partition made of rubber eliminates the gap therebetween, invasion of the flow into the cylinder during the sterilization process can be prevented and invasion of bacteria can be also prevented.

Embodiment 2

Figure 12:
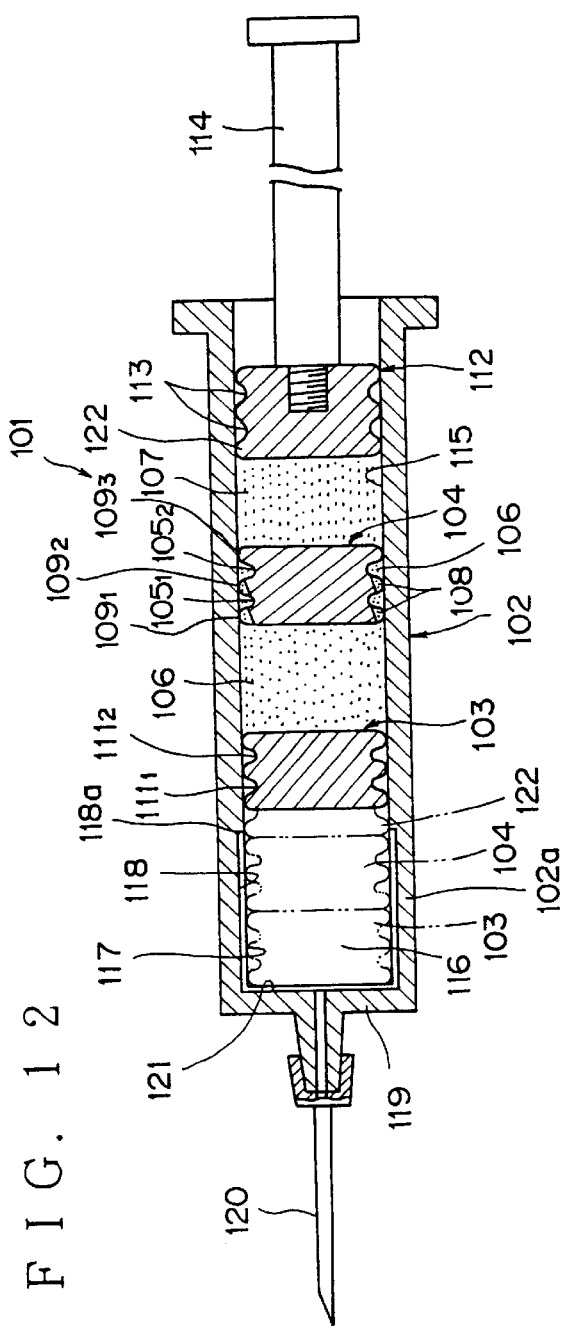
FIG. 12 is a longitudinal sectional view showing the second embodiment of the syringe according to the present invention.

FIG. 12 shows the second embodiment of a syringe according to the present invention.

A syringe 101 according to this embodiment is characterized in that it includes two partition stoppers 103 and 104 (made of rubber) arranged within a cylinder 102, along with an intermediate partition stopper 104 which is provided with communicating grooves 108 that communicate circular peripheral grooves $105_1$, $105_2$ with a first medicine solution 106. The peripheral grooves $105_1$ and $105_2$ are filled with the first medicine solution 106 from the communicating grooves 108.

Figure 13:
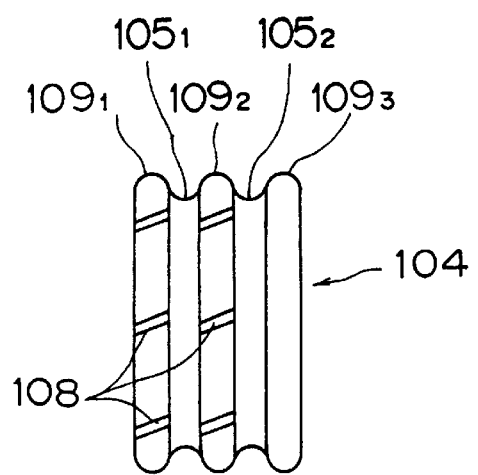
FIG. 13 is a front view showing an intermediate partition stopper build in the cylinder.
Figure 14:
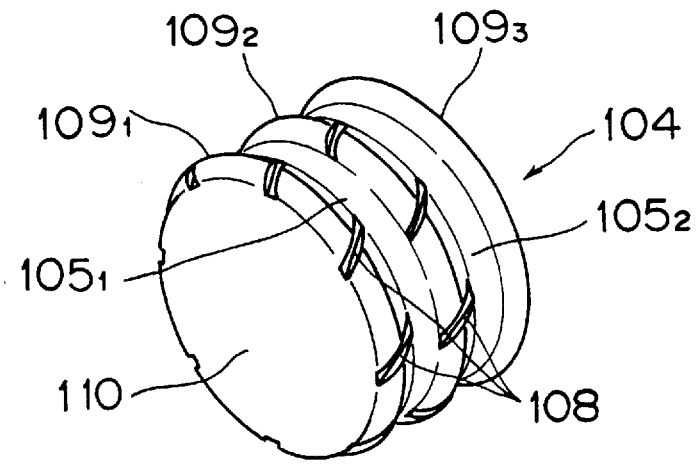
FIG. 14 is a perspective view showing the intermediate partition.

Specifically, the intermediate partition stopper 4, as shown in FIGS. 13 and 14, has the two peripheral grooves $105_1$, and $105_2$ between three circular lips $109_1$–$109_3$. Plural (six in the example shown) communicating grooves 108 are formed on the circular lip $109_1$ and the intermediate circular lip $109_2$ respectively. The communicating grooves 108 are formed slightly obliquely in a direction of thickness of the partition stopper 104 (axial direction), and have square sectional shapes. The circular lip $109_3$ on the other side of the partition stopper 104 is formed to have a diameter equal to those of the circular lip $109_1$ and the intermediate circular lip $109_2$, but has no communicating grooves. The outer peripheral surface of the circular lips $109_1$ to $109_3$ and the bottom surface of the peripheral grooves $105_1$ and $105_2$ have a semicircular shape (R-shape) as shown in FIG. 13. The peripheral grooves $105_1$ and $105_2$ serve to decrease the sliding resistance of the partition stopper 104 for the cylinder 102 as explained in connection with the prior art.

In this embodiment, the number of the circular lips $109_1$ to $109_3$ is three, but may be greater than three. Otherwise, a configuration having two circular lips and one peripheral groove therebetween may be proposed. In this case, the one circular lip has the same communicating groove as described above. Further, the communicating groove 108 may be formed not obliquely but straight in the direction of thickness of the partition stopper 104. The outer peripheral surface of the circular lips $109_1$ to $109_3$ and the bottom surface of the peripheral grooves $105_1$ and $105_2$ may have not a semicircular shape (R-shape) as shown in FIG. 13, but may be flat. In place of the communicating grooves 108, communicating holes which communicate the medicine solution 106 with the peripheral grooves $105_1$ and $105_2$ may be formed in the circular lips $109_1$ and $109_2$ or the trunk 110 of the intermediate stopper 104.

The intermediate partition stopper 104 is built in the cylinder 102 together with a front partition stopper 103 as shown in FIG. 12 by the vacuum filling/stopping technique as in the prior art. In this case, the peripheral grooves $105_1$ and $105_2$ are filled with the first medicine solution 106 through the communicating grooves 108 and air within the peripheral grooves $105_1$ and $105_2$ is displaced by the medicine solution 106 and sucked along the inner wall 115 of the cylinder.

The front partition stopper 103, which is formed to have a diameter and thickness equal to those of the intermediate partition stopper 104, has two peripheral grooves $111_1$ and $111_2$ like the intermediate partition stopper 104. The piston 112 behind the intermediate partition stopper 104, which is formed to have a larger thickness than that of the intermediate partition stopper 104, has also two peripheral grooves 113. In this embodiment, the front partition stopper 103 and the piston 112 has no communicating grooves unlike the intermediate partition stopper 104. A piston rod 114 is screwed to the piston. The circular lips $109_1$ and $109_2$ of the intermediate partition stopper 104 divided in a peripheral direction by the communicating grooves 108 are flexible enough to further decrease the sliding resistance.

In FIG. 12, if the intermediate partition stopper 104 is inserted (stopped) oppositely, the communicating grooves 108 are located on the side of the piston 112. In this case, during evacuation by the vacuum filling stopping technique, the peripheral grooves $105_1$ and $105_2$ are filled with the second medicine solution 107 from the communicating grooves 108. The intermediate partition stopper 104 may therefore be inserted oppositely.

At the front portion of the cylinder 102 of synthetic resin, a vacant chamber 116 is formed which can accommodate the front partition stopper 103 and the intermediate partition stopper 104. On the cylinder inner wall 117 of the vacant chamber 116, plural grooves 118 are formed in the longitudinal direction of the cylinder, and on the cylinder bottom wall 119, radiating grooves 121 communicating the grooves 118 with the syringe needle 120 are formed.

When the front partition stopper 103 is moved into the vacant chamber 116 by pushing the piston rod 114, the first medicine solution 106 passes through the grooves 118 and is supplied to the syringe needle 120 from the front of the vacant chamber 116. Further, when the intermediate partition stopper 104 is moved into the vacant chamber 116, the second medicine solution 107 is guided to the syringe needle 120 through the grooves 118 and 121. When both partition stoppers 103 and 104 have been completely moved into the vacant chamber 116, i.e., when injection has been finished, the front circular lip 122 of the piston 112 reaches the groove end 118a to stop.

Incidentally, the front portion 102a of the cylinder 102 including the vacant chamber 116 and the grooves 118, 121 may be made as a separate body which is to be connected to the cylinder body including the partition stoppers 103, 104 and piston 112. The cylinder front portion 102a and the cylinder body or the cylinder 102 may be made of either synthetic resin or glass.

The communicating grooves 108 may be formed on the intermediate and rear lips of the front partition stopper 103 or the front and intermediate lips of the piston 112. In this case, the peripheral grooves $111_1$ and $111_2$ are filled with the medicine solution 106, and the peripheral grooves 113 of the piston 112 is filled with the medicine solution 107. Further, air stagnancy in the cylinder is eliminated and mixing of bacteria in the air can be prevented. Nitrogen gas is sealed in the front vacant chamber 116.

In accordance with the second embodiment of the present invention, since in injection of medicine solution, the peripheral grooves of the partition stoppers or piston are filled with the medicine from the communicating portion (communicating grooves), no air is left in the peripheral grooves. For this reason, there is no fear of bacteria in the air invading the cylinder and two kinds of medicine solutions can be successively injected in one shot without pull-out/in of a syringe or ventilation. Thus, the discomfort of a patient caused by being repeatedly pricked with the syringe needle can be reduced and the work load on a doctor can be relieved.

Embodiment 3

FIGS. 15 to 22 show the third embodiment of the syringe according to the present invention.

Figure 15:
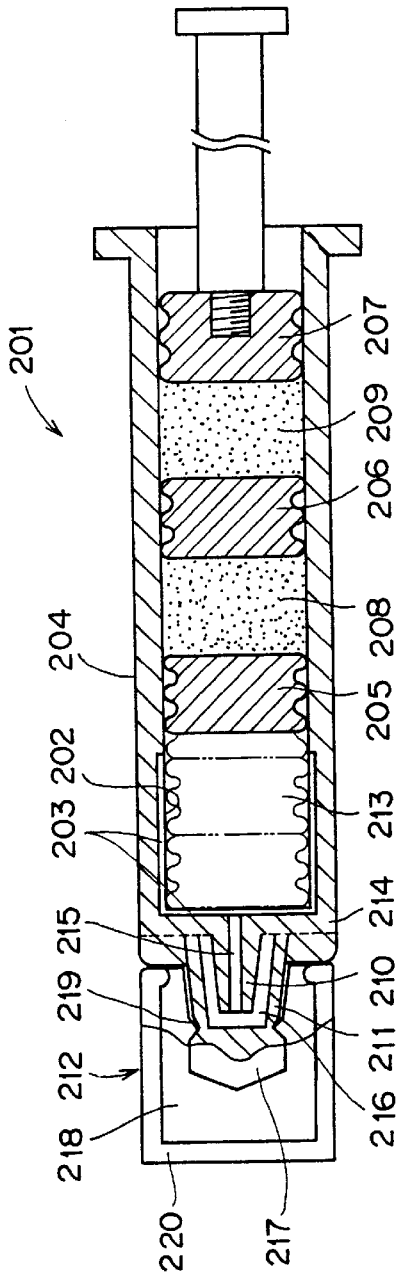
FIG. 15 is a longitudinal sectional view showing the third embodiment of the syringe according to the present invention.

A syringe 201, as shown in FIG. 15, includes a single cylinder type cylinder 204 of synthetic resin having communicating grooves 203 on a front inner wall 202, two partition stoppers 205, 206 (made of rubber) and a rear piston 207 slidably arranged within the cylinder 204, two kinds of medicine solutions 208 and 209 filled between the front partition stopper 205 and intermediate stopper 206 and between the intermediate partition stopper 206 and the rear piston 207, respectively, and a tip sealing portion 212 for water-proof and bacteria-proof formed integrally to a tapered protection external cylinder 211 peripherally formed outside of the cylindrical syringe needle connection portion 210 on the side of the syringe tip.

Figure 16:
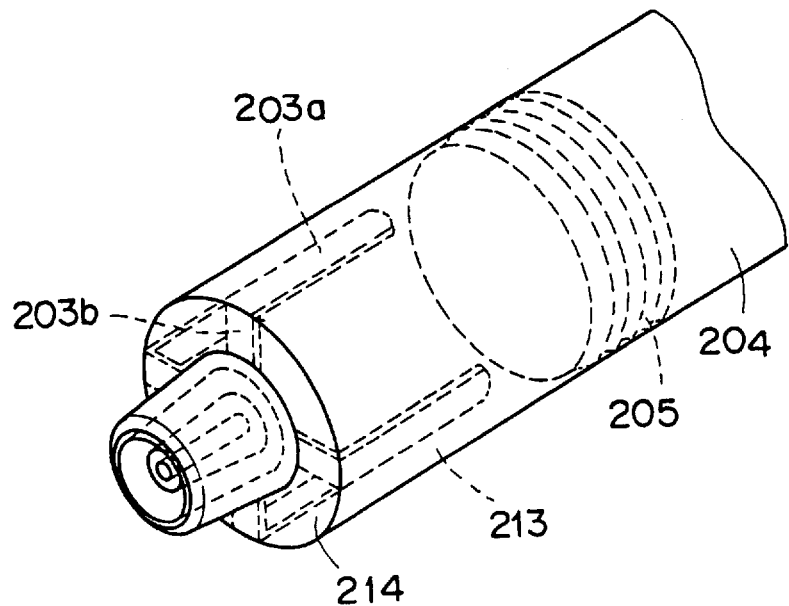
FIG. 16 is a perspective view showing the cylinder portion of the syringe.

The cylinder 204 is integrally molded of amorphous polyolefin (available as ZEONEX from Nihon Zeon Co. Ltd.). As shown in FIG. 16, on the inner wall of the front chamber 213, the above communicating grooves 203 are formed which includes four grooves 203a in a longitudinal direction and radiating grooves 203b which communicate the grooves 203a to a discharging hole 215 of the syringe needle connection portion 210. These communicating grooves 203 can be integrally formed in cylinder molding.

The amorphous polyolefin is generally excellent in gas-barrier property, absorbability (protein), dissolvability (chemical resistance), slidability (rubber stopper), and has most important features of moldablity, burnablity, light-weight and low cost, etc. Since it can be molded freely, grooves which cannot be formed using glass can be formed on the inner wall. Further, since the syringe is burnable, it can be disposed without producing industrial waste.

The front partition stopper 205 moves into the front space 213 by pushing the piston 207 so that the first medicine solution is discharged through the communicating grooves 203. Next, the intermediate partition stopper 206 moves into the front space 213 so that the second medicine solution 209 is similarly discharged. Thus, two kinds of medicine solutions can be injected by one shot. Although such a double separate-injection type structure is known in the conventional barrel-equipped syringe, this embodiment is characterized in that the communicating grooves 203 are formed in the integral single-cylinder type resin cylinder 204.

The cylinder 204 made of amorphous polyolefin has elasticity peculiar to synthetic resin and a mirror face like glass. This permits the syringe needle to be lure-locked with the syringe needle connection 210 and also permits the sliding valve and the piston to be slid with low friction. Since the cylinder 204 which is an integral type does not require the barrel to be mounted unlike before, inconvenience of flowing water invading the cylinder from an opening of the barrel during post-sterilization does not occur. Incidentally, PP (polypropylene) can be used in place of amorphous polyolefin. The cylinder made of these materials has also an advantage of low cost.

The front vacant chamber 213 in the cylinder 204, the discharge hole 215 of the syringe needle connection portion 210, the circular space 216 between the needle connection portion 210 and the external cylinder 211 are sealed with nitrogen gas. The nitrogen gas may be sealed at pressure slightly higher than atmospheric pressure. Thus, in unsealing the tip sealing portion 212 to mount a syringe needle in the needle connection portion 210, bacteria in a hospital are intercepted by the positive pressure of nitrogen gas so that they will not enter the cylinder 204. Further, the medicine 208 and the front vacant chamber 213 are partitioned by the front partition stopper 205 so that the medicine solution 208 is completely isolated from bacteria.

Figure 17:
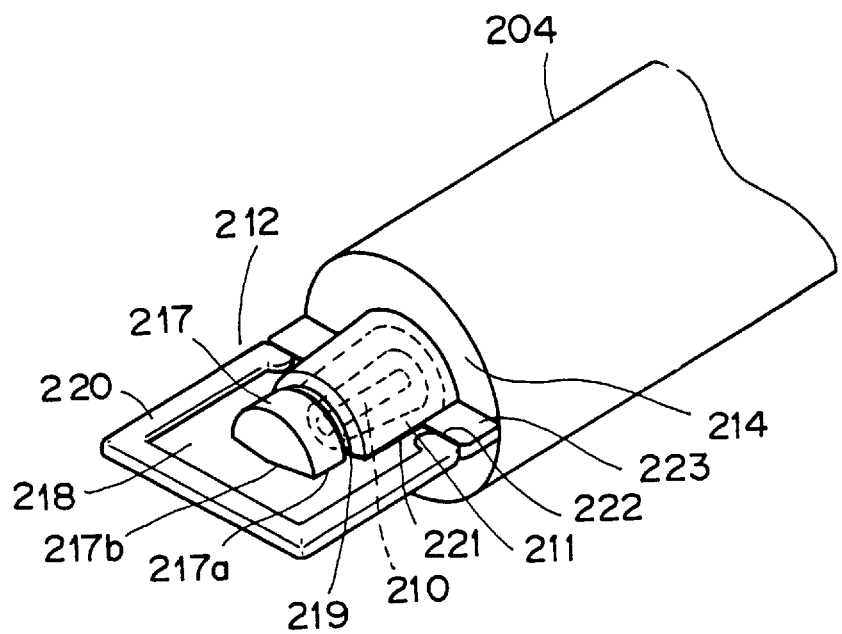
FIG. 17 is a perspective view of a first example of a sealing structure.
Figure 18A:
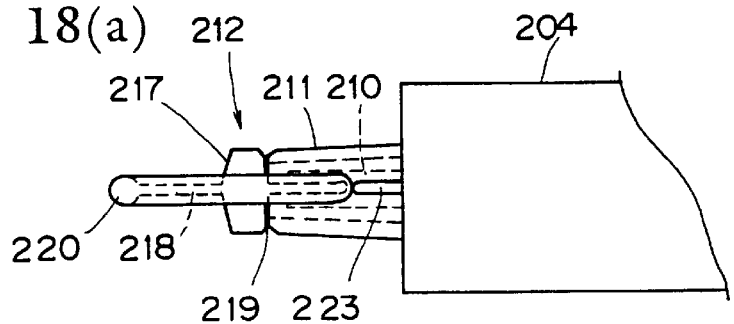

The tip sealing portion 212, as shown in FIGS. 17 and 18, includes: a cylindrical head 217 integrally continuous to the tip of the tapered external cylinder 211 outside the needle connection portion 210 through a circular recess groove 219; a thin twisting plate 218 successive to both sides 217a and the tip 217b of the head 217; and a thicker reinforcement frame 220 formed in the external periphery of the twisting plate 218. The boundary between the external cylinder 211 and the head 217 is formed to have the circular recess groove 219 having a wedge-shaped section and a small thickness. The twisting plate 218 is extended downwardly along the external cylinder 211 so that the inside makes a provisional junction (221) with the external cylinder 211 and the lower end makes another provisional junction (222) with a fin-shaped remaining portion 223 rising form the bottom 214 of the cylinder. The provisional junctions 221 and 222 are so adapted as to be easily separated when the twisting plate 218 is rotated. Incidentally, the remaining thickness portions 223 are not necessarily provided and the provisional junctions (221, 222) are not necessarily required.

The structure of the above tip hermetic sealing portion 212 is known as a profile seal system in a medicine solution package. The feature of the hermetic sealing structure according to the present invention resides in that said tip hermetic sealing is continuously formed to the protection external cylinder 211 for protection located outside the needle connection portion 210 so that the needle connection portion 210 is completely sealed and isolated from the outside. The external cylinder 211 is formed so as to protrude slightly higher than the needle connection portion 210 so that the needle connection portion 210 is not brought into contact with the head 217. Nitrogen gas is sealed within the circular space 216 surrounded by the head 217 and the external cylinder 211. The needle connection portion 210 is completely isolated from the outside by the head 217 and the external cylinder 211.

The tip hermetical-sealing portion 212 is made in actual fabrication in such a manner that it is attached to the external cylinder 211 by laser welding or ultrasonic-wave welding, or in a manner of double molding, i.e., molding the tip hermetic-sealing portion 212 by a second mold after molding the needle connection portion 210 by a first mold. Preferably, the external cylinder 211 has a diameter tapered toward the tip, and the tip 211a of the external cylinder 211, which has a possibly smaller diameter, is fixed toward the center of the head 217. This permits the twisting plate 218 to be operated by smaller force.

Figure 18B:
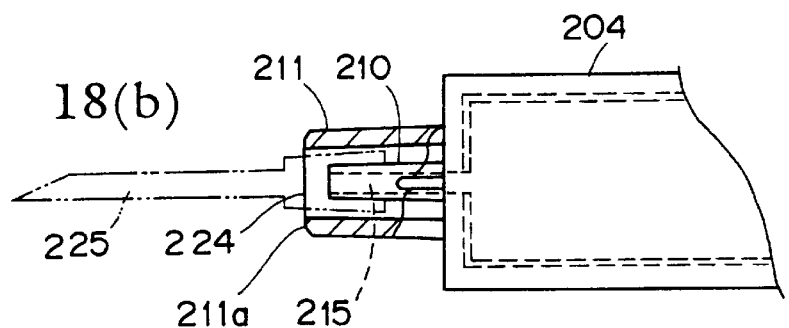

In use, a person engaged in medical treatment takes out the syringe 201 from a sterilization sack and twist the twisting plate 218 by fingers so that the provisional coupling portions 221 and 222 of the twisting plate 218 are separated and the head 217 rotates simultaneously with the twisting plate 218 so that it is separated from the tip 211a of the external cylinder 211. Thus, as shown in FIG. 18(b), the tip 211a of the external cylinder 211 is cut flatly (horizontally) to form a circular opening 224 at the tip 211a of the external cylinder 211. Even if bacteria in a hospital intends to invade the cylinder 204 simultaneously when the opening 224 is formed, the pressure of the nitrogen gas filled in the front vacant chamber 213 and discharging hole 215 stops the invasion. Subsequently, the syringe needle 225 in a separate sack is firmly fixed to the needle mounting (connection) portion 210 by lure-locking.

Figure 19:
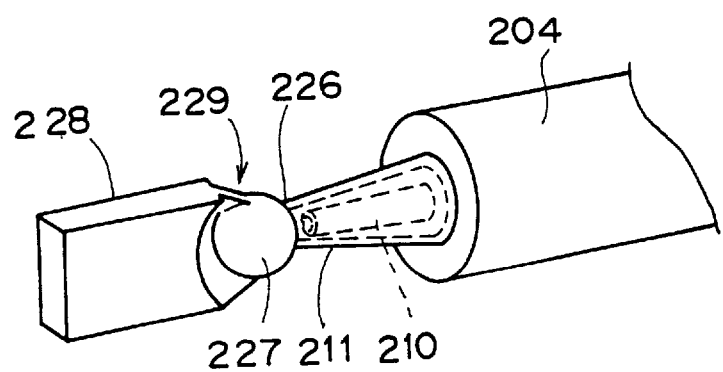
FIG. 19 is a perspective view showing the second example of the sealing structure.

FIG. 19 shows a first modification of the hermetic-sealing structure of the above syringe.

In this hermetic-sealing structure, a spherical head 227 is fixed, through a circular recess groove 226, to the tip of the external cylinder 211 outside the needle connection portion 210 of the cylinder 204 made of synthetic resin as in the above case, and a thick twisting plate 228 is provided to extend from the round head 227, thus completing a tip hermetic-sealing portion 229. This example is characterized in that the spherical head 227 is fixed to the tip of the tapered external cylinder 211 outside the needle connection portion 210 to seal the needle connection portion 210 on the inside of the external cylinder 211 completely. By twisting the twisting plate 228, the spherical head 227 is separated from the external cylinder 211 at the circular recess groove 226 so that the syringe needle 210 appears in the external cylinder 211.

Figure 20:
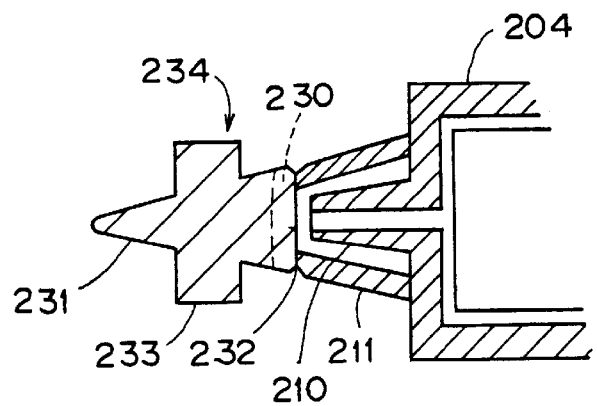
FIG. 20 is a longitudinal sectional view showing the third example of the sealing structure.
Figure 21:
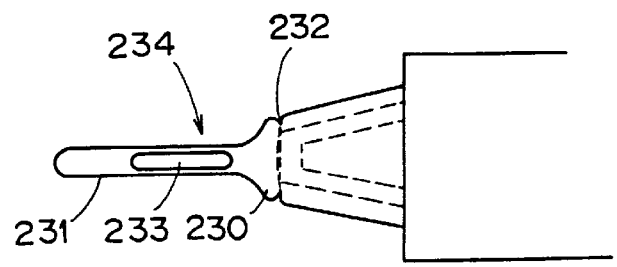
FIG. 21 is a plan view of the third example.

FIGS. 20 to 21 show a second modification of the hermetic-sealing structure of the kit-style syringe.

In this hermetic-sealing structure, a disk-shaped head 230 is connected to the tapered external cylinder 211 outside the needle connection portion 210 made of synthetic resin as in the above example, and a twisting plate 231 is protruded at the center of the disk-shaped head 230, thus completing a tip hermetic-sealing portion 234. The disk-shaped head 230 and the external cylinder 211 are connected integrally to each other through a circular recess groove 232 having a wedge section on the outside, and the flat twisting plate 231 is extended from the disk-shaped head 230. A pair of protruding plates 233 are integrated to the twisting plate 231. By twisting the protruding plates 233, the disk-shaped head 230 is cut along the circular recess groove 232 so as to be separated from the external cylinder 211. Thus, such a state results in that a syringe needle can be mounted in the needle mounting portion 210 in the external cylinder 211.

FIG. 22 shows a syringe with the tip hermetic-sealing portion 234. In this syringe 235, a communicating groove 238 as explained in the embodiment of FIG. 13 is formed in a front vacant chamber 237 of a cylinder 236 made of the amorphous polyolefin or resin such as PP, and an intermediate communicating groove 239 in a longitudinal direction is formed at the intermediate portion of the inner wall of the cylinder. A diluted solution 243 is accommodated between an intermediate partition stopper 241 behind the intermediate communicating groove 239 and a piston 242. Medicine powder 244 is accommodated between the intermediate partition stopper 241 and the front partition stopper 240. Since the cylinder 236 is integrally molded using resin, the intermediate communicating groove 239 does not bulge externally unlike the conventional cylinder made of glass. The cylinder itself has a smart design.

The nitrogen gas sealed in the front vacant chamber 237 of the cylinder 236 stops invasion of bacteria into the cylinder 236 together with the front partition stopper 240 when the tip sealing portion 234 is unsealed. In the syringe 235, when the piston 242 is pushed, the intermediate partition stopper 241 is located at the communicating groove 239, and the diluted solution 243 enters the intermediate chamber 245 through the intermediate communicating groove 239 to dissolve medicine powder 244. When the piston 242 is further pushed, the front partition stopper 240 is located on the communicating groove 238 so that the medicine solution is introduced into the discharge hole 246 through the communicating groove 238.

Each of the hermetic-sealing structure described above can be applied to not only a double layer type syringe with two partitions but also a single layer syringe using a single partition stopper, a syringe with no partition stopper but only a stopper or the conventional syringe with a barrel. In these cases, a configuration is desired whose front chamber is sealed with nitrogen gas and which has a front partition stopper.

In the third embodiments described above, the syringe needle connection portion is surrounded by the external cylinder and the tip hermetic-sealing portion so that it is completely sealed. For this reason, in post-sterilization or safe-keeping, viz., storage no water drops or bacteria can enter into the cylinder, while complete sanitization of the kit style syringe can be attained. In using the syringe, the twisting plate can be twisted to unseal the tip hermetic-sealing portion. Persons engaged in medical treatment is subjected to no burden. Further, in unsealing, the gas pressure in the cylinder and the front partition stopper stops invasion of bacteria from the syringe needle connection portion. Complete sanitization in using the syringe is attained. In addition, the resin integral cylinder can prevent invasion of vapor or bacteria from the cylinder intermediate portion as in the conventional barrel style syringe. The resin integral cylinder, which is combustible and inexpensive, can be readily disposed of. Since it is not used again, it is very sanitary. Further, since disinfection is not required, burden for persons engaged in medical treatment can be reduced.

[INDUSTRIAL APPLICABILITY]

As described above, in accordance with the first embodiment of the present invention, since the member equipped with the connection needle connection portion can be intimately coupled with the cylinder, invasion of bacteria from the junction between the member and cylinder can be prevented during safekeeping for a long time. In accordance with the second embodiment, since in injection of medicine solution, the medicine solution is filled in the peripheral grooves of the partition stopper and/or the piston through the communicating portion (communicating grooves), air does not remain in the peripheral grooves so that there is no fear of vacteria invading the cylinder. Further, in accordance with the third embodiment, since the syringe needle connection portion is completely hermetically sealed, water drops or vacteria will not be mixed into the cylinder from the syringe needle connection portion in sterilization using flowing vapor or safekeeping for a long time. The resin integral style cylinder solves the problem of invasion of vacteria water drops from the conventional cylinder intermediate portion and complete hermetic-sealing assures a very sanitary state. Further, in unsealing the syringe needle connection portion, the gas sealed in the cylinder and the front partition stopper commonly stop invasion of vacteria from the syringe needle connection portion so that in using the syringe, complete sanitization can be realized. In addition, since the resin integral style cylinder, which is combustible, can be disposed. Since it is not used again, it is very sanitary and burden for persons engaged in medical treatment is very slight. Accordingly, three rules of the kit style syringe, i.e., reduction in burden, prevention of mixing of alien substance and destruction of vacteria pollution can be realized in preparing medicine.

I claim:

1. A syringe comprising:
   a cylinder having first and second openings at first and second ends respectively;
   a communicating passage provided near the first opening, said communicating passage extending in an axial direction of said cylinder; and
   at least one slidable partition stopper disposed in said cylinder to define plural chambers within said cylinder; and a piston inserted through the second opening;

an elastic end partition having a radial passage, said end partition being intimately disposed in said cylinder proximate the first opening such that the radial passage communicates with said communicating passage, said end partition further including an axial passage which extends in an axial direction through said elastic end partition and which communicates with the radial passage; and a rigid syringe needle connection portion intimately disposed in the axial passage of said end partition.

2. A syringe according to claim 1, wherein said rigid syringe needle connection portion has a radially extending rotation preventing protrusion and wherein said end partition has fitting grooves corresponding to rotation preventing protrusion said.

* * * * *